United States Patent
Holms et al.

(10) Patent No.: US 6,171,814 B1
(45) Date of Patent: *Jan. 9, 2001

(54) PROCESS TO INCREASE THE PRODUCTION OF CLAVAM ANTIBIOTICS

(75) Inventors: William Henry Holms, Glasgow (GB); Ashish Sudhakar Paradkar; Roy Henry Mosher, both of Edmonton (CA)

(73) Assignees: SmithKline Beecham p.l.c., Brentford (GB); The Governors of the University of Alberta, Edmonton (CA)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/981,072
(22) PCT Filed: Jun. 6, 1996
(86) PCT No.: PCT/EP96/02497
  § 371 Date: May 11, 1998
  § 102(e) Date: May 11, 1998
(87) PCT Pub. No.: WO96/41886
  PCT Pub. Date: Dec. 27, 1996

(30) Foreign Application Priority Data

Jun. 9, 1995 (GB) .................................................. 9511679

(51) Int. Cl.[7] .......................... C12P 35/00; C12P 37/00; C12N 15/63; C12N 15/74
(52) U.S. Cl. ...................... 435/47; 435/193; 435/252.3; 435/252.33; 435/320.1; 435/471; 435/476; 435/477; 536/23.1; 536/23.2
(58) Field of Search ................................ 435/477, 471, 435/476, 193, 47, 252.3, 252.35, 320.1; 536/23.1, 232

(56) References Cited

U.S. PATENT DOCUMENTS 5,474,912 * 12/1995 Sherman et al. ...................... 435/43
5,705,340 * 1/1998 Rasmussen et al. ................... 435/6
5,756,326 * 5/1998 Martin et al. ....................... 435/471

FOREIGN PATENT DOCUMENTS 0349121 3/1990 (EP).
WO A
9418326 8/1994 (WO).

OTHER PUBLICATIONS

Romero, et al., "Isolation and Biochemical Characterization of *Streptomyces clavuligerus* Mutants in the Biosynthesis of Clavulanic Acid and Cephamycin C", *Appl. Microbiol. Biotechnol.*, 27:510–516.*

J.M. Wards et al., "The Biosynthetic Genes for Clavulanic Acid and Cephamycin . . . ", FEMS Microbiology Letters (1993) vol. 110, pp. 239–242.

H. Yu et al., "Possible Involvement of the Lat Gene in the Expression . . . ", Microbiology (1994), vol. 140, No. 12, pp. 3367–3377.

* cited by examiner

Primary Examiner—Ponnathapu Achutamurthy
Assistant Examiner—William W. Moore
(74) Attorney, Agent, or Firm—Zoltan Kerekes; Stephen Venetianer; Charles M. Kinzig

(57) ABSTRACT

A process for increasing the amount of clavam produced by an organism having both a clavam pathway or a portion thereof and a cephalosporin pathway or a portion thereof by interfering with the conversion of L-lysine to L-α-aminoadipic acid in the cephalosporin pathway. Plasmids containing a defective LAT (lysine amino transferase) gene and organisms containing such plasmids are also provided.

8 Claims, 1 Drawing Sheet

PROCESS TO INCREASE THE PRODUCTION OF CLAVAM ANTIBIOTICS

Figure 1A:
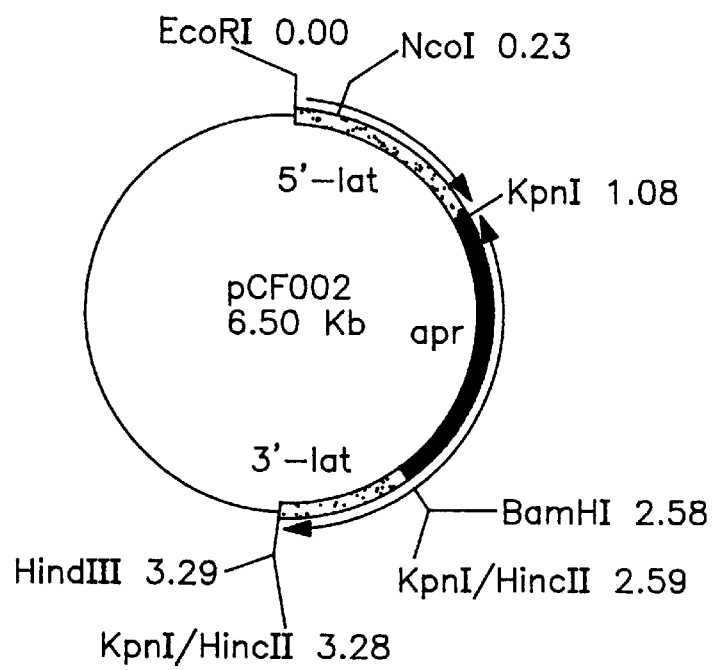

The present invention relates to processes for increasing the production of clavulanic acid and other clavams including those with strong β-lactamase inhibitory activity from producing organisms. The present invention also provides novel organisms capable of producing increased amounts of these clavams.

Microorganisms, in particular Streptomyces sp. produce a number of antibiotics including clavulanic acid and other clavams, cephalosporins, cephamycins, tunicamycin, holomycin and penicillins. There is considerable interest in being able to manipulate the absolute and relative amounts of these antibiotics produced and accordingly there have been a large number of studies investigating the metabolic and genetic mechanisms of these pathways [Domain, A. L. (1990) "Biosynthesis and regulation of beta-lactam antibiotics." In: 50 years of Penicillin applications, history and trends]. Many of the enzymes which carry out the various steps in the metabolic pathways and the genes which code for these enzymes are known.

In the cephalosporin metabolic pathway in, for example, *Strepromyces clavuligerus* three important antibiotics can be produced namely penicillin N, O-carbamoyldeacetylcephalosporin C and cephamycin C.

These antibiotics are synthesised from the tripeptide precursor d-(L-a-aminoadipyl)-L-cysteinyl-D-valine (ACV) [J. F. Martin et al (1990)., "Clusters of genes involved in Penicillin and cephalosporin biosynthesis" In: 50 years of penicillin applications history and trends].

The recognised first dedicated step in the biosynthesis of both penicillins and cephalosporins in *S. clavuligerus* involves the enzyme lysine -ϵ-amino transferase (LAT). The nucleotide sequence and derived amino acid sequence of *S. clavuligerus* lat gene is known [Tobin, M. B et al., (1991) J. Bacteriol, 173, 6223–6229].

U.S. Pat. No. 5,474,912 (published Dec. 12, 1995) describes a process for producing increased amounts of cephalosporins in *S. clavuligerus* by inserting one or more copies of a LAT gene into the chromosome of the organism. Although effects on β-lactam antibiotics are claimed, only effects on products of the cephalosporin pathway in *S. clavuligerus* are disclosed ie. no effects on clavam production were measured or described.

Clavulanic acid and other clavams are derived from a 3 carbon compound [Townsend, C. A. and Ho, M. F. (1985) J. Am. Chem. Soc. 107 (4), 1066–1068 and Elson, S. W and Oliver, R. S. (1978) J. Antiobiotics XXXI No.6, 568] and arginine [Valentine, B. P et al (1993) J. Am Chem. Soc. 15, 1210–1211].

The gene clusters which determine the biosynthesis of cephalosporins and clavulanic acid, although adjacent to each other on the *S. clavuligerus* chromosome [Ward, J. M. and Hodgson, J. E (1993) FEMS Microbiol. Lett. 110, 239–242] do not share common biosynthetic structural genes. Therefore there are no apparent biochemical links between the pathways.

Surprisingly we have found that when at least one step in the cephalosporin pathway of an organism is interfered with the amount of clavams produced by the organism is increased.

Accordingly the present invention provides a process for increasing the amount of clavam produced by an organism having both a clavam pathway or a portion thereof and a cephalosporin pathway or a portion thereof by interfering with the conversion of L-lysine to L-α-aminoadipic acid in the cephalosporin pathway.

Preferably the clavam has β-lactamase inhibitory activity and more preferably the clavam is clavulanic acid.

In a preferred aspect of the invention the process of conversion of L-lysine to L-α-aminoadipic acid is interfered with by altering the function of the LAT enzyme or the lat gene. For example the enzyme can be inhibited or otherwise blocked (for example by using a non-metabolisable substrate or analog).

Suitably the LAT gene can be obtained by conventional cloning methods (such as PCR) based on the published sequence. The function of the gene can be interfered with or eliminated/deleted by genetic techniques such as gene disruption [Aidoo, K. A. et al., (1994), Gene, 147, 4146]., random mutagenesis, site directed mutagenesis and antisense RNA.

Mahro, B. and Demain, A (1987), Appl.Microbiol. Technol. 27, 272–275 described a spontaneous mutant strain of *S. clavuligerus* (NP1) which did not produce cephamycin and was demonstrated to be defective in lat, acvs and ipns enzyme activities. H. Yu et al (1994) [Microbiology, 140, 3367–3377] demonstrated that the activity of these three enzymes can be recovered by transforming the mutant with a fragment of DNA encoding the entire LAT gene (lat) and the upstream half of the acvs gene (pcbAB). However there was no teaching of any effect in this mutant in relation to the production of clavulanic acid or other clavams.

In a further aspect of the invention there are provided plasmids containing a defective lat gene, preferably the plasmids pCF002 and p486latap described below. Suitably the plasmids are used to transform an organism such as *S. clavuligerus* eg strain ATCC 27064 (equivalent to *S. clavuligerus* NRRL 3585).

In a further aspect of the invention there is provided an organism containing a defective lat gene.

EXAMPLES

In the examples all methods are as in Sambrook, J., Fritsch, E. F. and Maniatis, T. (1989) Molecular Cloning A Laboratory Manual (2nd Edition) unless otherwise stated.

Example 1

Assembling the Disrupted lat Gene

To start the process pA2/119 (Thesis by A. K. Petrich (1993) Transcriptional analysis of the Isopenicillin N synthetase gene of *Streptomyces clavuligerus;* University of Alberta) was digested with KpnI to liberate its 0.688 kb insert. The digest was fractionated by agarose gel electrophoresis and the 0.688 kb fragment was eluted and Klenow-treated. The blunted fragment was then ligated to HincII-digested pUC119 and used to transform *E. coli* MV1193 to ampicillin resistance. A transformant, containing the recombinant plasmid hereinafter named pELK004 was isolated and its identity confirmed by restriction analysis. pELK004 was digested with BamHI and KpnI and ligated to a BamHI-KpnI apr$^r$-fragment. The ligation mixture was used to transform *E. coli* MV1193 to apramycin resistance. The resulting transformants were screened and a recombinant plasmid pCF001A containing the apr$^r$-fragment inserted upstream of, and inversely oriented to the 0.688-kb 3'-lat fragment was isolated and confirmed by restriction analysis.

In the next step pA2/119 was used as a template in a PCR reaction to subclone the upstream region of the lat gene into pUC119. The DNA primers used were the M13 reverse sequencing primer and a primer with the DNA sequence 5'CATGCGGATCCCGTCGACGAGCATATGC-3' SEQ.

LIST NO:1 under standard reaction conditions [PCR technology Principles and Applications for DNA amplification, Ed. H A Ehrlich (1989)] and a cycle composition of 92 degrees C for 30 s, 55 degrees C for 30 s and 72 degrees C for 60 s. PCR products were isolated by gel electrophoresis on a 1.25% agarose gel. The amplified DNA fragment was gel purified, digested with restriction endonucleases EcoR1 and BamH1, and ligated with similarly digested pUC119. Subsequent *E. coli* MV1193 transformants were analysed by restriction endonuclease treatment followed by gel electrophoresis and DNA sequence analysis to ensure that the correct fragment was cloned and that no unintended mutations were introduced during amplification by PCR. The pUC119 construction containing the DNA region upstream of lat was named pL/119.

The next step involved digesting pL1/119 with EcoR1 and Kpn1 to liberate its 1.08 kb fragment insert. The digest was fractionated by agarose gel electrophoresis and the 1.08 kb fragment was eluted and ligated to EcoR1 and Kpn1-digested pCF001A. The ligation mixture was used to transform MV1193 to apramycin resistance. The resulting transformants were screened and a clone was isolated that contained a recombinant plasmid pCF002 [see FIG. 1(*a*)] which possessed the 1.08 kb 5'-lat fragment upstream of the 3'-lat fragment, both in the same orientation, but separated from each other by the inversely oriented apr$^r$ fragment. The identity of pCF002 was confirmed by restriction analysis; the results indicated that the apr$^r$ fragment was inserted at the Kpn1 site, within the lat gene at 852 bp from the start codon and 521 bp from the stop codon.

Example 2

Introduction of the Disrupted lat Gene into *S. clavuligerus*

Figure 1B:
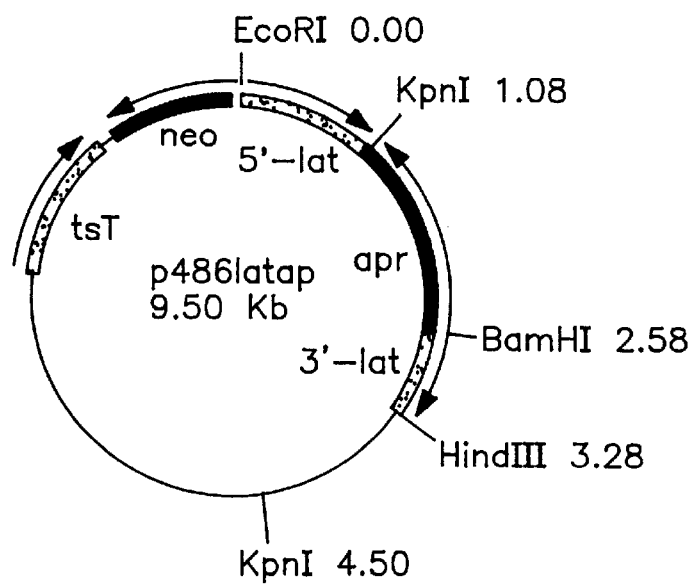

The disrupted lat gene was subcloned by digesting pCF002 with EcoR1 and HindIII (to liberate the DNA fragment carrying the disrupted lat gene) and ligating the digest with similarly digested pIJ486 to create p486latap [see FIG. 1(*b*)]. The ligation mixture was used to transform *S. lividans* protoplasts to apramycin resistance (Genetic Manipulation of Streptomyces. A Laboratory manual (1985) D. A. Hopwood et al.). A clone was selected that contained the recombinant plasmid p486latap; restriction analysis was then used to confirm the presence of the disrupted lat gene in p486latap.

p486latap was used to transform protoplasts of wild type *S. clavuligerus* (NRRL 3585) to apramycin resistance [Bailey, C. R and Winstanley, D. J J. Gen. Microbiol. (1986) 132, 2945–2947]. Only one transformant was obtained which grew up well when subcultured on MYM [Paradkar, A. S. and Jensen, S. E. (1994) J. Bact. 177, 1307–1314] supplemented with thiostrepton and apramycin The transformant was then subcultured to IPS medium #3 agar (unsupplemented) [Paradkar and Jensen, ibid] and allowed to sporulate at 28 degrees C. Spores were harvested and then replated for single colonies on to ISP medium #3 agar and MYM agar, both unsupplemented. These were allowed to sporulate and were then replica-plated successively on to MYM supplemented with thiostrepton, MYM supplemented with apramycin and MYM (unsupplemented). After three days at 28 degrees C colonies were apparent on the apramycin supplemented and unsupplemented plates but no colonies grew on the thiostrepton plates. Four of the apramycin resistant, thiostrepton sensitive colonies (lat#2, lat#5, lat#7 and lat#11) were selected for further investigation.

Because these isolates were apr$^r$, thio$^s$ it was assumed that a double cross-over event had occurred between p486latap and the *S. clavuligerus* chromosome. This assumption was confirmed by Southern hybridisation analysis.

Example 3

Cephamycin and Clavulanic Acid Production by the lat-disrupted Mutant

To determine the effect of the presumed lat disruption mutation on antibiotic production all four strains (disruptants) were grown in starch-asparagine (SA) liquid medium (Paradkar, A. S. and Jensen, S. E (1995), J. Bacteriol. 177, 1307–1314.) for 66 h at 28 degrees C. The supernatants were adjusted to account for different growth rates and then bioassayed against *E. coli* ESS (Paradkar and Jensen ibid.) and compared to similarly adjusted supernatants from cultures of wild type *S. clavuligerus*. Everyone of the lat-disruptants produced very small zones of inhibition corresponding to approximately 0.045 ug/ml/cephalosporins; under similar conditions the wild type strain was producing 3.18 ug/ml/cephalosporins.

Samples of the same supernatants were bioassayed for clavulanic acid production against *Klebsiella pneumoniae* (Bailey, C. R. et al. (1984) Bio/Technology 2(9) 808–811. All four disruptants appeared to produce two to three times the amount of clavulanic acid as compared to the wild type as judged by the bioassay.

Because all four of the lat disruptants seemed to exhibit similar phenotypes with respect to clavulanic acid production, and all four had been derived from one primary transformant, lat#2 was selected for further investigation. A time course experiment was carried out in which triplicate shake cultures of lat#2 and the wild type *S. clavuligerus* were grown in SA medium at 28 degrees C and sampled at 48 h, 72 h and 99 h after inoculation. Bioassay against *K. pneumoniae* showed that at 48 h, lat#2 was producing approximately four times the amount of clavulanic acid as the wild type. However by 99 h the lat#2 cultures were producing a little over twice as much clavulanic acid as the wild type. A concurrent bioassay of the same cultures for the same time periods against *E. coli* ESS showed that lat#2 produced no detectable antibacterial activity. Wild type cultures produced moderate but easily detectable amounts of cephalosporins (maximum titre 6.5 ug/ml)

Summary

A lat disruption mutant has been created. Experiments have shown that it produces negligible amounts of β-lactam antibiotics except clavulanic acid. Of the latter it produces at least two to three times the amount of clavulanic acid produced by wild type *S. clavuligerus* grown under shake flask conditions in Starch-Asparagine medium.

We claim:

1. A process for increasing the amount of clavam produced by an Actinomycete having both a clavam pathway or a portion thereof and a cephalosporin pathway or a portion thereof which comprises disrupting or eliminating a lat gene encoding an endogenous lysine-ε-amino transferase thereby preventing the conversion of L-lysine to L-α-aminoadipic acid in the cephalosporin pathway.

2. A process according to claim 1 wherein the clavam has β-lactamase inhibitory activity.

3. A process according to claim 2 wherein the clavam is clavulanic acid.

4. A recombinant plasmid containing a disrupted lat gene.

5. A plasmid according to claim 4 wherein the lat gene is disrupted by insertion of an apromycin resistance (aprr) fragment, which is carried on a vector selected from the group consisting of pUC119 and pIJ486.

6. A plasmid according to claim 5 wherein the apromycin resistance fragment is inserted into the lat gene at the KpnI site, 852 bp from the start codon and 521 bp from the stop codon.

7. An organism having both a clavam pathway or a portion thereof and a cephalo-sporin pathway or a portion thereof and containing a disrupted or mutated lat gene introduced in its chromosome.

8. An organism according to claim 7 which is *S. cla-vuligerus*.

* * * * *

SEQUENCE LISTING

<160> NUMBER OF SEQ ID NOS: 1

<210> SEQ ID NO 1
<211> LENGTH: 28
<212> TYPE: DNA
<213> ORGANISM: Artifical Sequence
<220> FEATURE:
<223> OTHER INFORMATION: PCR Primer

<400> SEQUENCE: 1
catgcggatc ccgtcgacga gcatatgc                    28